United States Patent
Carlisle

(10) Patent No.: US 10,327,998 B2
(45) Date of Patent: Jun. 25, 2019

(54) CELLULOSE CYANOACRYLATE AND METHOD OF EMPLOYMENT

(71) Applicant: Richard Sheldon Carlisle, Madrid, NY (US)

(72) Inventor: Richard Sheldon Carlisle, Madrid, NY (US)

(\*) Notice: Subject to any disclaimer, the term of this patent is extended or adjusted under 35 U.S.C. 154(b) by 0 days.

(21) Appl. No.: 15/944,698

(22) Filed: Apr. 3, 2018

(65) Prior Publication Data
US 2018/0256456 A1 Sep. 13, 2018

Related U.S. Application Data

(63) Continuation-in-part of application No. 15/238,748, filed on Aug. 17, 2016, now Pat. No. 9,988,509.

(51) Int. Cl.
| | |
|---|---|
| *A61K 6/027* | (2006.01) |
| *A61K 6/097* | (2006.01) |
| *C09J 4/00* | (2006.01) |
| *C09J 5/04* | (2006.01) |

(52) U.S. Cl.
CPC ............ *A61K 6/097* (2013.01); *A61K 6/0273* (2013.01); *A61K 6/0276* (2013.01); *C09J 4/00* (2013.01); *C09J 5/04* (2013.01); *C09J 2400/20* (2013.01); *C09J 2401/006* (2013.01)

(58) Field of Classification Search
CPC .... A61K 6/097; A61K 6/0273; A61K 6/0276; A61K 6/0032; A61K 6/0023; A61K 6/007; A61K 6/0014; C09J 5/00; C09J 5/04; C09J 2400/20; C09J 2401/006

USPC ................ 442/286, 444, 394; 156/281, 336; 604/304; 606/60; 433/29

See application file for complete search history.

(56) References Cited

U.S. PATENT DOCUMENTS

| | | | | |
|---|---|---|---|---|
| 4,743,468 | A | * 5/1988 | Jimenez | B29C 73/02 156/94 |
| 6,296,604 | B1 | * 10/2001 | Garibaldi | A61B 17/12022 600/12 |
| 8,152,750 | B2 | * 4/2012 | Vournakis | A61L 15/44 600/490 |
| 2006/0008499 | A1 | * 1/2006 | Hudak | A61L 24/001 424/423 |

\* cited by examiner

*Primary Examiner* — Pedro Philogene

(57) ABSTRACT

Cellulose cyanoacrylate is employed to bond two surfaces, fill voids or duplicate the shape of a three-dimensional object, Two surfaces may be bonded by placing a sheet of cellulose material between the surfaces and applying cyanoacrylate glue around the edge of the sheet until saturated and allowing it to cure. Paper toweling may favorably be employed as the cellulose material. A break or fracture in an article can be overlaid with a sheet of cellulose that when saturated with cyanoacrylate glue and temporarily held in place and shaped with a releasable film, the fracture can be corrected. A dry powder comprising highly abrasion-resistant particles can be mixed with the cellulose material to enhance abrasion resistance and to improve long-term color stability—especially important for dental cavity treatment. To duplicate the shape of a three-dimensional object, a sheet of releasable film is placed over the object, followed by a sheet of cellulose that is then saturated with cyanoacrylate glue. A sheet of releasable film is then placed over the cellulose and used to hold the cellulose in place and shape it as it hardens.

14 Claims, No Drawings

CELLULOSE CYANOACRYLATE AND METHOD OF EMPLOYMENT

An invention is provided for repairing a wide variety of broken items made of plastic, wood or metal and is useful for copying or forming original three-dimensional prototypes and art objects, similar to the methodology of fiberglass.

The method involves employing a new compound called cellulose cyanoacrylate, formed by saturating fibrous sheets of cellulosic material, e.g., including cotton and paper toweling made of wood fibers, with cyanoacrylate glue including one or more of cyano-methyl, cyano-ethyl and cyano-octyl acrylates.

The cyanoacrylate-saturated cellulose can be used as an overlay on a broken area of anything in need of repair and held in place momentarily with a thin film of release material such as polyethylene that does not adhere to the glue-saturated cellulose.

The saturated cellulose can be used as an overlay on a broken or cracked area of nearly any item. The saturated cellulose sheet can be held in place momentarily using a thin film of a release material, such as polyethylene that does not adhere to the glue-saturated cellulose. While serving for temporary retention, the release material facilitates manipulating the shape of the cellulose before hardening, by applying pressure by manual or mechanical means. The release film also plays an important role in preventing emission of inhaling fumes and vapors that form during the exothermic reaction between the cellulose and the cyanoacrylate compounds.

Additionally, assuming it does not disrupt the eventual configuration of the repaired object, one or several layers of cellulose sheet—preferably paper toweling—can be placed between the surfaces to be joined and then holding the pieces together add enough cyanoacrylate glue, e.g., on the edges, to soak through the cellulose, which in itself in some cases can be sufficient as a repair without need for an exterior overlay.

To duplicate a three-dimensional object a layer of releasable film is placed around it or a silicone spray applied, followed by a cellulose sheet that is then saturated in place with cyanoacrylate glue and then another external layer of releasable film is added through which to press the cellulose snugly around the shape being duplicated. After cure, the resulting cellulose cyanoacrylate compound can be removed and employed to duplicate the shape of the three-dimensional object.

A kit or combination for the repair of cracked or fractured articles can include one or more sheets of cellulosic material, e.g., an absorbent paper or similar wood product; a container of any type of cyanoacrylate glue; and one or more sheets of flexible film, e.g., a polyethylene film which does not adhere to the cured cyanoacrylate. This kit can also be used to duplicate the shape of a three-dimensional article.

The advantages of the invention include:
1) Very brief cure or hardening times—ordinarily faster than thirty seconds—compared to epoxy times of one to several minutes.
2) Extreme tolerance to moisture, allowing it to function as a dental repair material as well as a great variety of underwater applications.
3) Pleasant pearl-like translucent appearance.
4) Very light weight-to-strength ratio.
5) Flexible and spring-like consistency.
6) Readily made in any color.
7) Very hard, abrasion-resistant surface.
8) Can be used for orthopedic work to repair and/or reinforce bones, i.e., at a fracture site. In many cases this technique can be used after taking the usual steps to make the wound area sterile and surgically making the fracture site available, to avoid the use of plates, pins or screws. This technique includes repositioning and wrapping a bone fracture with two layers of paper towel or similar cellulose sheet, saturating with cyanoacrylate, and adding separately two additional layers at a time to achieve a desired strength. The cellulose sheet can be of a width between four and fifty millimeters and a thickness of one half millimeter up to three milimeters. At each stage, the saturated layers are covered with a release film and gentle pressure can be applied to exclude air pockets or bubbles and also to shape the material. Before closing up the wound site the release material is removed. The repair material can be left intact indefinitely, allowing the bone to knit and thereafter permanently providing support and making the bone stronger than was originally. A major advantage is the reduced need for an external cast or other support system.
9) Any irritant or fumes can be controlled easily. During the relatively short cure period, after infusing the cellulose material with cyanoacrylate glue, any vapors can be confined by covering the materials with a non-pervious film that is releasable and can be removed after the components have reacted sufficiently.

Cellulose Cyanoacrylate for Dentistry

Two important uses for the cellulose cyanoacrylate compound for dentistry are: 1) Treatment of cavities caused by anaerobic bacteria producing exo-toxins that erode enamel and dentin, and 2) Restoration of teeth missing portions of their structure.

In Applicant's experiments using cellulose cyanoacrylate for dental fillings it was discovered that an anti-bacterial effect takes place that reduces the amount of drilling ordinarily required to remove all bacteria, thus resulting in less loss of tooth structure.

The bacteria residing in the cavity are therefore eliminated and prevented from regenerating due to an apparent residual antibacterial effect.

The best form of cellulose to use for tooth cavity repair is cotton wool with a pH value of 6 (plus or minus 2) mixed with liquid cyanoacrylate: preferably a blend of methyl and ethyl cyanoacrylates.

The cotton wool can be enhanced significantly by mixing it with high-abrasion-resistant powdered minerals like quartz, or glass—very finely pulverized, of the type used be dentists for composite fillings.

The advantages of the powder and cotton mixture are: increased abrasion resistance, better color and translucent match with adjacent tooth surface and improved stability of color long term, along with the fact the cavity does not have to be thoroughly dry before filling, since the cellulose cyanoacrylate during its curing process can absorb water and use it for a curing catalyst.

The method of treating a cavity includes minimal drilling, wherein loose material resulting from bacterial action is removed, but some active bacteria can remain, soon to be removed by the antibacterial action of the curing process. Some additional drilling can then undercut the cavity wall for secure retention of the filling material Method of Filling Dental Cavities:
1) Line the cavity with a thin coating of liquid cyanoacrylate cement.

2) Quickly insert powder-infused cotton wool and add liquid cyanoacrylate glue to saturate the filling.
3) Add a final layer of powder-infused cotton, if necessary, and saturate it with liquid cyanoacrylate.
4) Apply pressure through a thin, flexible layer of releasable film comprising, for example, polyethylene or aluminum foil to remove air spaces and provide a relatively consistent texture throughout the filling.
5) In some cases it may be more convenient to saturate the filling material first, rather than inserting it dry. This necessitates using polyethylene tweezers to hold the glue-saturated filling to avoid sticking to the tweezers, or, gripping the filling with releasable film wrapped partly around the filling material. In any event, polish the final surface with a diamond-dust bit in a rotary drill device.

For restoration procedures to replace major portions of teeth, a sheet form of cellulose substantially comprising wood pulp fibers—similar to paper towels—is ideal where relatively large, smooth surfaces are required. In this case, the cellulose sheet should have the pulverized powder thoroughly interspersed before placing on the tooth and saturating with cyanoacrylate glue, followed by applying pressure through a flexible releasable film.

Another enhancement of cellulose cyanoacrylate consists of incorporating one or more layers of stainless steel mesh in direct contact with one or more layers of the compound. In experimental trials the mesh that was used had a porosity of 100 per inch and a thickness of 6 one thousandths of an inch. Tensile strength can be increased dramatically with this enhancement along with improvements in shear and bending strength.

I claim:

1. A fibrous cellulose material interspersed with finely pulverized abrasion-resistant particles and when saturated with liquid cyanoacrylate glue produces a waterproof, germicidal, high-abrasion-resistant cellulose cyanoacrylate compound with long-term color stability for dental cavity filling and restoration of teeth.

2. The fibrous cellulose material of claim 1 is natural cotton wool.

3. The fibrous cellulose material of claim 1 is in sheet form substantially comprising wood pulp fibers.

4. The fibrous cellulose material of claim 1, wherein, the liquid cyanoacrylate glue is selected from the group comprising methyl, ethyl, propyl, butyl, pentyl, hexyl, septyl, octyl, nonyl and decyl.

5. The fibrous cellulose material of claim 1, wherein, the liquid cyanoacrylate glue is any combination of the types of cyanoacrylate glue.

6. The fibrous cellulose material of claim 1, wherein, the abrasion-resistant particles are selected from the group: glass, quartz and other highly abrasion-resistant minerals.

7. The fibrous cellulose material of claim 1, wherein, the compound is adapted as a filling material for a dental cavity after the cavity is lined with a coating of liquid cyanoacrylate glue.

8. The fibrous cellulose material of claim 1, wherein, the compound is adapted to fill a dental cavity without having to remove all bacteria from the cavity.

9. The fibrous cellulose material of claim 1, wherein, the compound is combined with a layer of flexible release material for the smoothing and forming of the compound after it is in place inside a dental cavity.

10. A fibrous cellulose material containing highly abrasion-resistant particles and adapted for saturation with liquid cyanoacrylate glue to form a waterproof cellulose cyanoacrylate compound surrounding said particles for the filling of voids.

11. The fibrous cellulose material of claim 10, wherein, the particles are selected to match the color of an article with voids to be filled with the compound.

12. The fibrous cellulose material of claim 10, wherein, the cellulose material is colored to match the color of an article with a void(s) to be filled.

13. The fibrous cellulose material of claim 10, wherein, the saturated fibrous cellulose material is held with tweezers made at least partly of releasable material that does not stick to the saturated cellulose after placing said cellulose in position.

14. An assemblage of material containing at least one layer of fibrous cellulose adapted to be saturated with liquid cyanoacrylate glue to form a waterproof, abrasion-resistant cellulose cyanoacrylate compound in combination with at least one layer of metal mesh for reinforcement.

* * * * *